US011759544B2

(12) United States Patent
Farmer et al.

(10) Patent No.: US 11,759,544 B2
(45) Date of Patent: Sep. 19, 2023

(54) THERAPEUTIC COMPOSITIONS FOR ENHANCED HEALING OF WOUNDS AND SCARS

(71) Applicant: Locus Solutions IPCo, LLC, Solon, OH (US)

(72) Inventors: Sean Farmer, North Miami Beach, FL (US); Ken Alibek, Solon, OH (US); Albina Tskhay, Solon, OH (US)

(73) Assignee: LOCUS SOLUTIONS IPCO, LLC, Solon, OH (US)

( * ) Notice: Subject to any disclaimer, the term of this patent is extended or adjusted under 35 U.S.C. 154(b) by 0 days.

(21) Appl. No.: 16/965,353

(22) PCT Filed: May 24, 2019

(86) PCT No.: PCT/US2019/033989
§ 371 (c)(1),
(2) Date: Jul. 28, 2020

(87) PCT Pub. No.: WO2019/227034
PCT Pub. Date: Nov. 28, 2019

(65) Prior Publication Data
US 2021/0121597 A1 Apr. 29, 2021

Related U.S. Application Data

(60) Provisional application No. 62/824,387, filed on Mar. 27, 2019, provisional application No. 62/676,444, filed on May 25, 2018.

(51) Int. Cl.
A61L 15/36 (2006.01)
A61P 17/02 (2006.01)
A61K 31/6615 (2006.01)
A61K 35/66 (2015.01)
A61K 36/064 (2006.01)
A61K 36/886 (2006.01)
A61K 45/06 (2006.01)
A61L 15/26 (2006.01)
A61L 15/38 (2006.01)
A61L 15/40 (2006.01)
A61L 15/44 (2006.01)

(52) U.S. Cl.
CPC .......... *A61L 15/36* (2013.01); *A61K 31/6615* (2013.01); *A61K 35/66* (2013.01); *A61K 36/064* (2013.01); *A61K 36/886* (2013.01); *A61K 45/06* (2013.01); *A61L 15/26* (2013.01); *A61L 15/38* (2013.01); *A61L 15/40* (2013.01); *A61L 15/44* (2013.01); *A61P 17/02* (2018.01)

(58) Field of Classification Search
CPC .. A61K 31/6615; A61K 35/66; A61K 36/064; A61K 36/886; A61K 45/06; A61L 15/26; A61L 15/36; A61L 15/38; A61L 15/40; A61L 15/44
See application file for complete search history.

(56) References Cited

U.S. PATENT DOCUMENTS

| 4,902,512 | A | 2/1990 | Ishigami et al. |
| 5,487,899 | A * | 1/1996 | Davis ............ A61K 36/886 424/443 |
| 5,981,497 | A | 11/1999 | Maingault |
| 6,403,108 | B1 | 6/2002 | Abdullah |
| 8,361,778 | B2 | 1/2013 | Bergmaier |
| 10,065,982 | B2 | 9/2018 | Hirata et al. |
| 2003/0050277 | A1 | 3/2003 | Kajimoto et al. |
| 2007/0116750 | A1* | 5/2007 | Wolcott ............ A61K 47/42 424/445 |
| 2009/0071493 | A1 | 3/2009 | Nguyen et al. |
| 2009/0203649 | A1 | 8/2009 | Kato et al. |
| 2010/0216197 | A1 | 8/2010 | Shiraishi et al. |
| 2011/0044972 | A1 | 2/2011 | Fieldhouse et al. |
| 2011/0135616 | A1 | 6/2011 | Girard et al. |
| 2011/0237531 | A1 | 9/2011 | Yanagisawa et al. |
| 2013/0331466 | A1 | 12/2013 | Gross et al. |
| 2014/0127257 | A1 | 5/2014 | Schiemann et al. |
| 2014/0323757 | A1 | 10/2014 | Kim |
| 2014/0364381 | A1* | 12/2014 | Ju ............ A61L 15/44 514/25 |

(Continued)

FOREIGN PATENT DOCUMENTS

| CN | 102078282 A | 6/2011 |
| CN | 103800224 A | 5/2014 |

(Continued)

OTHER PUBLICATIONS

Gharaei-Fathabad, E., "Biosurfactants in Pharmaceutical Industry (A Mini-Review)." American Journal of Drug Discovery and Development, 2011, 1(1): 58-69.
Rowan, M. P., et al., "Burn Wound Healing and Treatment: Review and Advancements." Critical Care, 2015, 19(1): 1-12.
Shen, C., et al., "Targeted Killing of Myofibroblasts by Biosurfactant di-rhamnolipid Suggests a Therapy Against Scar Formation." Scientific Reports, 2016, 6(1): 1-10.
Tiwari, V. K., "Burn Wound: How it Differs from Other Wounds?" Indian Journal of Plastic Surgery, 2012, 45(2): 364-373.
Bhadoriya, S.S., et al., "Biosurfactants: A New Pharmaceutical Additive for Solubility Enhancement and Pharmaceutical Development." Biochemistry & Pharmacology: Open Access, 2013, 2(2): 1-5.

(Continued)

*Primary Examiner* — Ali Soroush
(74) *Attorney, Agent, or Firm* — SALIWANCHIK, LLOYD & EISENSCHENK

(57) ABSTRACT

The subject invention provides topical therapeutic compositions and methods of their use for enhanced healing of wounds, including burns, and scars of the skin. Specifically, in one embodiment, the subject invention provides materials and methods for reducing the healing time of skin wounds and for reducing the appearance of scars. The subject invention utilizes topical compositions comprising microbial growth by-products and, optionally, a topically-acceptable carrier. In specific embodiments, the microbial growth by-products are biosurfactants.

15 Claims, No Drawings

(56) References Cited

U.S. PATENT DOCUMENTS

| | | |
|---|---|---|
| 2015/0037302 A1 | 2/2015 | Bralkowski et al. |
| 2016/0083757 A1 | 3/2016 | Fonseca et al. |
| 2016/0101211 A1 | 4/2016 | Zimnitsky et al. |
| 2016/0199530 A1 | 7/2016 | Ploeger et al. |
| 2016/0213757 A1 | 7/2016 | Edelson et al. |
| 2016/0235661 A1 | 8/2016 | Changoer et al. |
| 2016/0309715 A1 | 10/2016 | Diaz de Rienzo et al. |
| 2016/0324747 A1 | 11/2016 | Ito et al. |
| 2017/0071842 A1 | 3/2017 | Schelges et al. |
| 2017/0087199 A1 | 3/2017 | Patron et al. |
| 2017/0119638 A1 | 5/2017 | Kondo et al. |
| 2017/0172913 A1 | 6/2017 | Ballesteros et al. |
| 2019/0231668 A1 | 8/2019 | Yoo et al. |
| 2019/0307788 A1 | 10/2019 | Wakayama |

FOREIGN PATENT DOCUMENTS

| | | | |
|---|---|---|---|
| CN | 104178538 A | 12/2014 | |
| CN | 105567580 A | 5/2016 | |
| CN | 105886572 A | 8/2016 | |
| DE | 10131796 A1 * | 1/2003 | ............ A61Q 19/00 |
| EP | 0540074 A1 | 5/1993 | |
| EP | 1212093 | 6/2002 | |
| EP | 1228752 A2 | 8/2002 | |
| EP | 1964546 A1 | 9/2009 | |
| EP | 2351847 A1 | 8/2011 | |
| JP | 2007129973 A | 5/2007 | |
| JP | 2009029788 A * | 2/2009 | |
| JP | 2012051872 A | 3/2012 | |
| KR | 20110012699 A | 2/2011 | |
| PT | 106959 A * | 11/2014 | ............ C12P 19/44 |
| RU | 2185147 C2 | 7/2002 | |
| WO | 9850523 A1 | 11/1998 | |
| WO | 2004020647 A1 | 3/2004 | |
| WO | 2012088276 A2 | 6/2012 | |
| WO | 2013112875 A1 | 8/2013 | |
| WO | 2014120247 A1 | 8/2014 | |
| WO | 2015153476 A1 | 10/2015 | |
| WO | 2016117489 A1 | 7/2016 | |
| WO | 2017044953 A1 | 3/2017 | |
| WO | WO-2017051433 A1 * | 3/2017 | ............ A61K 9/0014 |
| WO | 2018049182 A2 | 3/2018 | |
| WO | 2018129299 A1 | 7/2018 | |
| WO | 2018191174 A1 | 10/2018 | |
| WO | 2018208530 A1 | 11/2018 | |
| WO | 2019022997 A1 | 1/2019 | |
| WO | 2019023039 A2 | 1/2019 | |
| WO | 2019075456 A3 | 4/2019 | |
| WO | 2019089730 A1 | 5/2019 | |
| WO | 201913313 A1 | 7/2019 | |
| WO | 2019133315 A1 | 7/2019 | |
| WO | 2019133555 A1 | 7/2019 | |
| WO | 2019140439 A1 | 7/2019 | |
| WO | 2019140440 A1 | 7/2019 | |
| WO | 2019191293 A1 | 10/2019 | |
| WO | 2019200054 A1 | 10/2019 | |
| WO | 2019222168 A1 | 11/2019 | |
| WO | 2020006194 A1 | 1/2020 | |
| WO | 2020041261 A1 | 2/2020 | |

OTHER PUBLICATIONS

Ciesielska, K., et al., "Exoproteome analysis of Starmerella bombicola results in the discovery of an esterase required for lactonization of sophorolipids." Journal of proteomics, 2014, 98: 159-174.

Coronel-Leon, J., et al., "Optimizing the production of the biosurfactant lichenysin and its application in biofilm control." Journal of Applied Microbiology, 2015, 120: 99-111.

De Brito, D., Biosurfactants from renewable raw materials, Universidade do Minho Departamento de Engenharia Biológica, Nov. 2013, pp. 1-93.

De Oliveira, M., et al., "Review: Sophorolipids A Promising Biosurfactant and it's Applications." International Journal of Advanced Biotechnology and Research, 2015, 6(2): 161-174.

Ines, M., et al., "Glycolipids biosurfactants; potential related biomedical and biotechnical applications." Carbohydrate Research, 2015, 416: 59-69.

Kim, K., et al., "Characteristics of Sophorolipid as an Antimicrobial Agent." J. Microbiol. Biotechnol., 2002, 12(2): 253-241.

Kurtzman, C.P., et al., "Production of sophorolipid biosurfactants by multiple species of the Starmerella (Candida) bombicolayeast clade." FEMS Microbiol Lett, 2010, 311: 140-146.

Ma, X., et al., "Surface and biological activity of sophorolipid molecules produced by Wickerhamiella domercqiae var. sophorolipid CGMCC 1576." Journal of Colloid and Interface Science, 2012, 376: 165-172.

Santos, D.K.F., et al., "Biosurfactants: Multifunctional Biomolecules of the 21st Century." International Journal of Molecular Sciences, 2016, 17(401): 1-31.

Sen, R., "Biosurfactants: Advances in Experimental Medicine and Biology." Landes Bioscience and Springer Science+Business Media, LLC, 2010, 672: 1-331.

Sharma, A., et al., "A New Triterpenoid Saponin and Antimicrobial Activity of Ethanolic Extract from Sapindus mukorossi Gaertn." Journal of Chemistry, 2013, 2013: 1-5.

Sil, J., et al., "Health Care Applications of Different Biosurfactants: Review." International Journal of Science and Research, Oct. 2017, 6(10): 41-50.

Takahashi, M., et al., "Production of Sophorolipid Glycolipid Biosurfactants from Sugarcane Molasses Using Starmerella bombicola NBRC 10243." Journal of Oleo Science, 2011, 60(5): 267-273.

Torres Faria, N., et al., "Production of glycolipid biosurfactants, mannosylerythritol lipids, from pentoses and D-glucose/D-xylose mixtures by Pseudozyma yeast strains." Process Biochemistry, 2014, 49(11): 1790-1799.

* cited by examiner

THERAPEUTIC COMPOSITIONS FOR ENHANCED HEALING OF WOUNDS AND SCARS

CROSS-REFERENCE TO RELATED APPLICATIONS

This application is a National Stage Application of International Application No. PCT/US2019/033989, filed May 24, 2019; which claims priority to U.S. Provisional Patent Application Ser. No. 62/676,444, filed May 25, 2018; and Ser. No. 62/824,387, filed Mar. 27, 2019, each of which is incorporated by reference herein in its entirety.

BACKGROUND

A wound is an injury to tissue caused by a cut or other form of impact. Wounds can be closed (e.g., a contusion, a closed fracture), or open (e.g., a cut, abrasion, ulcer, lesion, crush, scrape, puncture, tear, burn, laceration, surgical incision, gunshot wound, bite, sting or avulsion).

With burn wounds, in particular, the wound may be an injury caused by heat, cold, electricity, chemicals (e.g., acids or bases), friction, or radiation (e.g., sunburn). First-degree burns are usually limited to redness (erythema), a white plaque, and minor pain at the site of injury. These burns usually extend only into the epidermis. Burns filled with clear fluid, having superficial blistering of the skin, and involving more or less pain depending on the level of nerve involvement, are second degree burns. Second-degree burns involve the superficial (papillary) dermis and may also involve the deep (reticular) dermis layer.

Burns having charring of the skin and producing hard leather-like eschars are third degree burns. An eschar is a scab separated from the unaffected part of the body. Frequently, there is also purple fluid and/or pus. Nerve endings, hair follicles and sweat glands may be lost. Third degree burns often result in scarring.

Fourth, fifth and sixth degree burns can include charring and/or total loss of skin, muscle and/or bone, and can be fatal in some instances.

The healing of wounds and burns can be a lengthy and continuous process, although it is typically recognized as occurring in stages. The process begins immediately after injury with an inflammatory stage. During this stage, which typically lasts from two days to one week, damaged tissues and foreign matter are removed from the wound. Blood vessels constrict and seal off as platelets create substances that form clots and halt bleeding. The blood vessels then dilate after hemostasis is achieved, and allow nutrients, white blood cells, antibodies and enzymes to enter the affected area to promote healing and prevent infection.

Following, and overlapping with the inflammatory response, the proliferative stage is characterized by fibroblast proliferation and collagen and proteoglycan production. During this stage, extracellular matrix is synthesized in order to begin the closing of the wound and to provide structural integrity to the tissue. The body turns damaged mesenchymal cells into fibroblasts to serve as bridges and to help cells move around the affected area. These fibroblasts, or myofibroblasts, produce and deposit collagen to help strengthen the wound. The proliferative stage usually lasts about four days to several weeks. It is during this stage when hypertrophic scars usually form.

Overlapping with the proliferative phase, the final phase of healing involves remodeling the wound. During the remodeling stage, the previously constructed and randomly organized granular tissue matrix is remodeled into an organized structure that is highly cross-linked and aligned to increase mechanical strength. The wound scar matures as collagen and elastin are deposited and continuously produced as fibroblasts become myofibroblasts. Myofibroblasts adopt a contractile phenotype, and thus are involved in wound contracture. The conversion from fibroblasts to myofibroblasts controls a delicate balance between contraction and re-epithelialization that, in part, determines the pliability of the repaired wound. In addition to fibroblast conversion, apoptosis of keratinocytes and inflammatory cells are key steps in the termination of wound healing and the overall final appearance of the wound. Remodeling can take as long as two years or more.

Although burns are different from other wounds in some respects, healing of all wounds involves the dynamic processes described above. The healing of a burn wound can take a significant amount of time, and frequently occurs with discomfort, pain and scarring. Like other wounds, the amount of time a burn wound requires to heal depends on the depth and severity of the burn. For example, with some, more serious burns, the wounded tissue may be excised and re-grafted with a skin graft. This may prolong the healing process. (Rowan et al. 2015).

In many cases, a wound, including a burn wound, may heal with scarring. Scars can be benign, but in some instances, they can be abnormal or excessive, leading to pain, immobility, loss of functionality and/or an unaesthetic appearance. Conditions resulting from excessive scarring or the abnormalities in wound healing include, e.g., fibrosis, fibromatosis, keloidosis, adhesions (e.g., surgical adhesions), hypertrophic scars, fibrocystic conditions, and joint stiffness. Contractures can also occur, where the skin surrounding a wound is pulled together by myofibroblasts in a way that can lead to severe restriction of mobility. (Tiwari 2012).

In the formation of an abnormal scar, in some cases, more collagen is produced than is degraded, which can also occur alongside an over-production of extracellular matrix components, cells, fibronectin, elastin, and proteoglycan. Therefore, the scar grows larger than is required for wound healing. Alternatively, collagen can be inadequately replaced and, as a result, the skin can form a pitted appearance.

For hypertrophic scars, the underlying pathophysiology of formation is not well known. Hypertrophic scars are a side effect of excessive wound healing, and generally result in the overproduction of cells, collagen, and proteoglycans. Failure for granulation tissue deposition to decrease as the active healing cells are suppressed in the proliferation stage often results in the arrangement of fibroblasts, small vessels, and collagen fibers into a nodular pattern. Typically, these scars are raised and are characterized by the random distribution of tissue bundles. The appearance (i.e., size, shape, and color) of these scars varies depending on the part of the body in which they form, and the ethnicity of the person affected. Hypertrophic scars are very common, and may occur following any full thickness injury to the skin.

Keloids can also form during the proliferation stage, where overgrowth of granulation tissue is more extreme than with hypertrophic scars. Keloids are typically characterized as tumors consisting of highly hyperplastic masses that occur in the dermis and adjacent subcutaneous tissue, most commonly following trauma. They are firm, rubbery lesions or shiny, fibrous nodules that are elevated above the skin. Keloids are often more severe than hypertrophic scars, as they tend to invade normal adjacent tissue, while hypertrophic scars tend to remain confined within the original scar border.

Scarring that results from burns, compared with most other traumatic wounds, can be more extensive due to a greater surface area of injury. Deep dermal burns, if not excised and grafted are almost certain to develop hypertrophic scarring. Many burn patients require long-term treatment for scars, with complications including itching, dryness, ulcerations, sensitivity to sun and chemicals and emotional problems related to appearance.

Generally, methods for treating scars and keloids are costly, with low probability of success. For example, treatments can include surgical excision followed by graft application, with a risk of new scars being developed after the excisions, or pressure bandages, which typically require maintaining a pressure of at least 25 mm Hg for approximately six months to achieve a visual effect. Other treatments include ionizing radiation therapy; application of silicone pads to the scar tissue surface, sometimes under pressure provided by an elastomeric bandage; topical application of silicone gel sheets, with or without added vitamin E; topical or intra-lesional treatment with corticosteroids; and various pharmaceutical creams, powders, and beads that interfere with the proteins known to be involved in wound healing, skin growth and scar formation. As such, many attempts have been made to improve scar healing and reduce the adverse aesthetic effects of scarring, but without great success or convenience.

Thus, injury to skin as a result of surgery, trauma, pathological conditions, burns, sports injuries and the like, typically heal in a manner that leaves scarring. While such scarring is often undesirable aesthetically, it can also result in other adverse effects, including loss of function, restriction of movement, reduced skin elasticity and potentially a reduced quality of life. Despite the attempts made to date to provide a method for facilitating healing of a skin wound such as to reduce scarring, there exists a continuing need for improvement in this respect.

Accordingly, there is a need for pharmaceutical formulations to treat skin conditions that improve wound, burn and scar healing processes. Furthermore, there is a strong need for a skin treatment that addresses both the healing and cosmetic aspects of skin management, which minimizes the curing times of wounds, including minor burns, and the development of scars therefrom.

BRIEF SUMMARY

The present invention provides microbe-based products, as well as methods of their use, in topical therapeutic compositions. More specifically, the subject invention provides methods for promoting the healing of wounds, including burns, while reducing the appearance of scars, using compositions comprising microbial growth by-products. Advantageously, the compositions and methods of the subject invention are non-toxic and cost-effective.

In preferred embodiments of the present invention, a topical therapeutic microbe-based composition for enhanced healing of wounds and/or scars is provided, wherein the composition comprises one or more microorganisms and/or microbial growth by-products. Methods of producing the microorganisms and their growth by-products are also provided.

In certain embodiments, the microbial growth by-products are amphiphilic molecules (e.g., biosurfactants), enzymes and/or proteins. In one embodiment, the microbial growth by-products have antimicrobial and/or anti-biofilm properties. In one embodiment, the microbial growth by-products have skin rejuvenating properties, meaning they help make skin appear, e.g., younger, smoother and brighter.

In a preferred embodiment, the composition comprises one or more amphiphilic molecules, wherein the amphiphilic molecules are biosurfactants selected from, for example, low molecular weight glycolipids (e.g., sophorolipids, rhamnolipids, cellobiose lipids, mannosylerythritol lipids and trehalose lipids), lipopeptides (e.g., surfactin, iturin, fengycin, arthrofactin and lichenysin), flavolipids, phospholipids (e.g., cardiolipins), fatty acid ester compounds, fatty acid ether compounds, and high molecular weight polymers such as lipoproteins, lipopolysaccharide-protein complexes, and polysaccharide-protein-fatty acid complexes.

The one or more biosurfactants can further include any one or a combination of: a modified form, derivative, fraction, isoform, isomer or subtype of a biosurfactant, including forms that are biologically or synthetically modified.

In one embodiment, the one or more biosurfactants are present in the composition in critical micelle concentration (CMC). In certain embodiments, the one or more biosurfactants are isolated and/or purified.

In certain embodiments, the biosurfactants according to the present invention are capable of enhancing dermal penetration of active and inactive ingredients in the composition; thus the biosurfactants can enhance the effectiveness of the treatment while serving as active ingredients.

In one embodiment, the biosurfactants include sophorolipids (SLP) and/or mannosylerythritol lipids (MEL). In one embodiment, the biosurfactants include cardiolipins (CL).

In one embodiment, a combination of SLP, MEL and CL are utilized in the composition, wherein the SLP and MEL serve as, for example, healing agents, and the CL serve as, for example, skin rejuvenating agents.

In some embodiments, the composition comprises live or inactivated microorganisms capable of producing growth by-products useful for skin healing and rejuvenation. In certain embodiments, the microorganisms are yeasts, such as, e.g., *Starmerella bombicola, Wickerhamomyces anomalus, Meyerozyma (Pichia) guilliermondii,* and/or *Pseudozyma aphidis.*

In one embodiment, the composition can further comprise a dermatologically-acceptable carrier, such as a water-in-oil or oil-in-water emulsion, or an aqueous serum.

The composition may have other components including, for example, carriers, pH modifiers, buffers, local anesthetic agents, agents that promote wound healing, agents that help degrade biofilm, anti-microbial agents, agents that stop bleeding and/or promote clot formation, and other therapeutic and non-therapeutic components known to, e.g., heal, replenish, rejuvenate, moisturize, protect and/or improve the healing, appearance and/or functioning of the skin. For example, in certain embodiments, the composition can further comprise vitamins, minerals, botanicals, extracts, essential oils, retinoids, anti-comedo agents, moisturizers, and/or sunscreens.

In some embodiments, the topical composition can further comprise adjuvants and additives typically found in topical skin care compositions, such as, for example, organic solvents, silicones, stabilizers, thickeners, softeners, dyes or fragrances.

In certain embodiments, the subject invention provides methods to promote the healing of a skin condition, wherein a topical therapeutic composition of the subject invention is applied directly to an area of the skin where such a condition exists. In preferred embodiments, the skin condition is a wound, including burns, or a scar.

According to the subject invention, "promotion" of healing means enhancing, or accelerating the rate of healing, and/or otherwise creating conditions at the site of the skin condition that favor healing thereof.

In some embodiments, "applying" the composition comprises leaving the composition on the wound or scar, and/or rubbing it in so that the composition is absorbed into the area completely. In some embodiments, the composition is applied to the skin for a therapeutically-effective amount of time and then rinsed or removed from the skin using, for example, water or a cloth. In yet other embodiments, the composition is applied using a breathable polymer matrix, which can be impregnated with the composition and used as a dressing or cover for the wound or scar.

In certain embodiments, the topical therapeutic composition is applied, e.g., every other day, once daily, up to ten times daily. In some embodiments, the topical composition is applied every other day, once daily, up to ten times daily, for an indefinite period of time, e.g., for at least one, two, three weeks, or longer, until the wound or scar is healed.

The topical compositions and methods of the subject invention can be used to promote the healing of wounds categorized as open wounds, including burns and burn-related irritation, blisters and rashes. Preferably, the wound has passed the inflammatory phase of healing and has entered the proliferative phase of healing or a later phase of healing.

Additionally, the topical compositions and methods of the subject invention can be used to promote the healing of scars (e.g., hypertrophic scars, acne scars, contractures and/or keloids). For example, the subject invention can be used to ameliorate or reduce the appearance and/or presence of a scar, or ameliorate or reduce the negative effects of a scar, such as immobility, pain or itching.

DETAILED DESCRIPTION

The present invention provides microbe-based products, as well as methods of their use, in topical therapeutic compositions. More specifically, the subject invention provides methods for promoting the healing of wounds, including burns, while reducing the appearance of scars, using compositions comprising microbial growth by-products. Advantageously, the compositions and methods of the subject invention are non-toxic and cost-effective.

In preferred embodiments of the present invention, a topical therapeutic microbe-based composition for enhanced healing of wounds and/or scars is provided, wherein the composition comprises one or more microorganisms and/or microbial growth by-products. Methods of producing the microorganisms and their growth by-products are also provided.

In certain embodiments, the microbial growth by-products are amphiphilic molecules (e.g., biosurfactants), enzymes and/or proteins. In one embodiment, the microbial growth by-products have antimicrobial and/or anti-biofilm properties. In one embodiment, the microbial growth by-products have skin rejuvenating properties, meaning they help make skin appear, e.g., younger, smoother and brighter.

In certain embodiments, the subject invention provides methods to promote the healing of a skin condition, wherein a topical therapeutic composition of the subject invention is applied directly to an area of the skin where such a condition exists. In preferred embodiments, the skin condition is a wound, such as a burn, or a scar.

Selected Definitions

As used herein, the term "healing" refers to eradication, reduction, amelioration or reversal of a sign or symptom of a condition or disorder to any extent or degree, and includes, but does not require, a complete cure of the condition or disorder.

As used herein, "preventing" a condition or disorder refers to avoiding, delaying, forestalling, or minimizing the onset of a particular sign or symptom of the condition or disorder. Prevention can, but is not required to be, absolute or complete, meaning the sign or symptom may still develop at a future time. Prevention can include reducing the severity of the onset of such a condition or disorder, and/or inhibiting the progression of the condition or disorder to a more severe condition or disorder.

As used herein, "promoting" means enhancing, improving, or accelerating the rate at which an intended effect occurs. For example, promoting wound healing can mean improving the skin's healing process by hastening the speed thereof, preventing scarring and/or otherwise creating conditions at the site of the wound that favor healing thereof. As another example, promoting scar healing can mean reducing the size or visibility of the scar, reducing the negative symptoms associated with the scar (e.g., in the case of a keloid or contracture) and/or otherwise creating conditions at the site of the scar that favor healing thereof.

As used herein, the term "wound" refers to an injury to tissue caused by, for example, a cut, blow or other impact. According to the subject invention, wounds include injuries to the skin, categorized as "open wounds," and include, for example, cuts, abrasions, ulcers, lesions, scrapes, crushes, punctures, tears, burns, lacerations, incisions, gunshot wounds, bites, stings and avulsions.

As used herein, the term "burn" refers to a wound caused by thermal (heat or cold), chemical (e.g., from an acid or base), friction, radiation (e.g., sunburn or UV), or electrical sources. A burn may be a "minor" burn, which includes first-degree burns with superficial damage to the outer dermis layer, and second-degree burns, with damage extending down into the epidermal layer of cells. Symptoms of burns include, for example, irritation, blistering, itching, peeling, rashes, redness, and swelling.

As used herein, the term "scar" refers to a mark or growth on the skin where an injury, e.g., a wound, burn, sore, surgical incision or piercing, has not healed properly and fibrous connective tissue has developed in place of normal tissue. Scars can include hypertrophic scars, where an overproduction of collagen creates an area of raised tissue above the surrounding skin; keloids, another form of excessive scarring where the tissue forms into large, protruding neoplasms; atrophic scars, where underlying structural tissue is lost, resulting in a pitted or sunken appearance (e.g., acne scars); and stretch marks, resulting from rapid stretching of the skin during, e.g., pregnancy, growth spurts or skin regeneration.

In addition to promoting the healing of wounds, including burns, and/or scars, other uses for the subject invention may include the treatment and/or prevention of, for example, other skin conditions. As used herein, the term "skin condition" encompasses any human and animal conditions, disorders, or diseases affecting the integument, or skin. Such skin conditions include, but are not limited to, conditions involving the epidermis, dermis (including connective tissue, sebaceous glands and hair follicles), and the subcutaneous tissue (hypodermis). Skin conditions that can, in certain embodiments, be treated and/or prevented using compositions, products and methods described herein include, but are not limited to, wounds (including, e.g., burns), scars, acne, blemishes, rosacea, folliculitis, carcinoma, melanoma, perioral dermatitis, cellulitis, carbuncles, photodamage, skin aging (e.g., wrinkles and dryness), age spots, psoriasis, ichtiosis, atopic dermatitis, rashes (including but not limited to erythematosus, macular, papular and/or bullous conditions), chronic wounds, bed sores, keratosis piralis, sebaceous cysts, vitiligo, melisma, warts, inflammatory dermatoses, allodynia, ectopic dermatitis, telangiectasia, post-inflammatory hyperpigmentation, keratoses, eczema, xerosis, pruritis, lichen planus, nodular prurigo, microbial infection, body odor, scalp conditions and miliaria. Symptoms of skin conditions can include, for example, skin irritation/sensitivity, blemishes and other acneiform symptoms, pigmentation or loss thereof, flushing, inflammation, wrinkles, dryness, looseness, thickening, scaling, scarring, flaking, rash, hives, blisters, ulcers, peeling, hair loss and other changes in the health, function and appearance of the skin.

As used herein, the term "subject" refers to an animal, preferably a mammal. The preferred subject in the context of this invention is a human. The subject can be of any gender and any age or stage of development including infant, toddler, adolescent, teenager, young adult, middle-aged, or senior.

As used herein, "topical" means suitable for local application externally to the skin, or cutaneous application. In other words, a topical composition is not intended for application to a subject via oral, intravenous, intramuscular, intrathecal, subcutaneous, sublingual, buccal, rectal, vaginal, inhalation, ocular or otic routes.

As used herein, "dermatologically-acceptable," "cosmetically-acceptable" and "topically-acceptable" are used interchangeably and are intended to mean that a particular component is safe and non-toxic for application to the integument (e.g., skin) at the levels employed. In one embodiment, the components of the composition are recognized as being Generally Regarded as Safe (GRAS).

As used herein, the terms "therapeutically-effective amount," "effective amount," and "effective dose" are used to refer to an amount of something (e.g., a compound, a composition, time) that is capable of achieving a desired amount of healing in a subject. The actual amount will vary depending on a number of factors including, but not limited to, the particular condition or disorder requiring healing, the severity of the condition, the size, age, and health of the subject, and the manner of administration.

As used herein, a "microbe-based composition" means a composition that comprises components that were produced as the result of the growth of microorganisms or other cell cultures. Thus, the microbe-based composition may comprise the microbes themselves and/or by-products of microbial growth (e.g., biosurfactants, solvents and/or enzymes). The cells may be in a vegetative state or in spore form, or a mixture of both. The cells may be planktonic or in a biofilm form, or a mixture of both. The cells may be live or inactive, intact or lysed. The cells can be removed from the medium in which they were grown, or present at, for example, a concentration of at least $1\times10^4$, $1\times10^5$, $1\times10^6$, $1\times10^7$, $1\times10^8$, $1\times10^9$, $1\times10^{10}$, or $1\times10^{11}$ or more cells per milliliter of the composition. In one embodiment, the microbe-based composition may comprise only the medium in which the cells were grown, with the cells removed. The by-products of growth may be present in the medium and can include, for example, metabolites, cell membrane components, expressed proteins, and/or other cellular components. In one embodiment, the microbe-based composition comprises only microbial growth by-products.

The subject invention further provides "microbe-based products," which are products that are to be applied in practice to achieve a desired result. The microbe-based product can be simply the microbe-based composition harvested from the microbe cultivation process. Alternatively, the microbe-based product may comprise further ingredients that have been added. These additional ingredients can include, for example, stabilizers, buffers, carriers, and other additives and/or adjuvants suitable for a particular application. The microbe-based product may also comprise mixtures of microbe-based compositions. The microbe-based product may also comprise one or more components of a microbe-based composition that have been processed in some way such as, but not limited to, filtering, centrifugation, lysing, drying, purification and the like.

A "metabolite" refers to any substance produced by metabolism (e.g., a growth by-product) or a substance necessary for taking part in a particular metabolic process. Examples of metabolites include, but are not limited to, enzymes, acids, solvents, alcohols, proteins, carbohydrates, vitamins, minerals, microelements, amino acids, polymers, and biosurfactants.

As used herein, the terms "isolated" or "purified," when used in connection with biological or natural materials such as nucleic acid molecules, polynucleotides, polypeptides, proteins, organic compounds, such as small molecules, microorganism cells/strains, or host cells, means the material is substantially free of other compounds, such as cellular material, with which it is associated in nature. That is, the materials do not occur naturally without these other compounds and/or have different or distinctive characteristics compared with those found in the native material.

In certain embodiments, purified compounds are at least 60% by weight the compound of interest. Preferably, the preparation is at least 75%, more preferably at least 90%, and most preferably at least 99% or 100% (w/w) of the desired compound by weight. Purity is measured by any appropriate standard method, for example, by column chromatography, thin layer chromatography, or high-performance liquid chromatography (HPLC) analysis.

As used herein, an "isomer" refers to a molecule with an identical chemical formula to another molecule, but having unique structures. Isomers can be constitutional isomers, where atoms and functional groups are bonded at different locations, and stereoisomers (spatial isomers), where the bond structure is the same but the geometrical positioning of atoms and functional groups in space is different. MEL isomers, for example, can differ in bond type and bond location of the carbohydrate, fatty acid and/or acetyl groups.

As used herein, "surfactant" means a surface-active substance, or a compound that lowers the surface tension (or interfacial tension) between two liquids or between a liquid and a solid. Surfactants act as, e.g., detergents, wetting agents, emulsifiers, foaming agents, and/or dispersants. By "biosurfactant" is meant a surfactant produced by a living cell.

The transitional term "comprising," which is synonymous with "including," or "containing," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention. Use of the term "comprising" contemplates other embodiments that "consist" or "consist essentially of" the recited component(s).

Unless specifically stated or obvious from context, as used herein, the term "or" is understood to be inclusive. Unless specifically stated or obvious from context, as used herein, the terms "a," "an" and "the" are understood to be singular or plural.

Unless specifically stated or obvious from context, as used herein, the term "about" is understood as within a range of normal tolerance in the art, for example, within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein. Other features and advantages of the invention will be apparent from the following description of the preferred embodiments thereof, and from the claims. All references cited herein are hereby incorporated by reference.

Topical Therapeutic Compositions

The subject invention provides skin care compositions and methods of their use. In particular, the subject invention provides therapeutic skin care products that can treat and/or prevent a skin condition, including wounds and scars, and/or others described herein.

In certain embodiments, the present invention utilizes microbial growth by-products. Particularly, embodiments of the present invention provide a topical therapeutic composition for promoting the healing of skin conditions, wherein the composition comprises therapeutically-effective amounts of one or more biochemicals produced by the cultivation of microorganisms.

In certain embodiments, the microbial growth by-products are amphiphilic molecules, enzymes and/or proteins. In one embodiment, the microbial growth by-products have antimicrobial and/or anti-biofilm properties. In one embodiment, the microbial growth by-products have skin rejuvenating properties, meaning they help make skin appear younger, smoother and brighter.

In a preferred embodiment, the composition comprises one or more amphiphilic molecules, wherein the amphiphilic molecules are biosurfactants selected from, for example, low molecular weight glycolipids (e.g., sophorolipids, rhamnolipids, cellobiose lipids, mannosylerythritol lipids and trehalose lipids), lipopeptides (e.g., surfactin, iturin, fengycin, arthrofactin and lichenysin), flavolipids, phospholipids (e.g., cardiolipins), fatty acid ester compounds, fatty acid ether compounds, and high molecular weight polymers such as lipoproteins, lipopolysaccharide-protein complexes, and polysaccharide-protein-fatty acid complexes.

Biosurfactants are surfactants produced by living cells. They are amphiphiles, consisting of two parts: a polar (hydrophilic) moiety and non-polar (hydrophobic) group. Due to their amphiphilic structure, biosurfactants reduce the surface and interfacial tensions between the molecules of liquids, solids, and gases.

Additionally, biosurfactants accumulate at interfaces, thus leading to the formation of aggregated micellar structures in solution. The ability of biosurfactants to form pores and destabilize biological membranes permits their use as, e.g., antibacterial and antifungal agents. Furthermore, biosurfactants are biodegradable, have low toxicity, and can be produced using low-cost renewable resources. They can inhibit microbial adhesion to a variety of surfaces, prevent the formation of biofilms, and can have powerful emulsifying and demulsifying properties.

The one or more biosurfactants can further include any one or a combination of: a modified form, derivative, fraction, isoform, isomer or subtype of a biosurfactant, including forms that are biologically or synthetically modified. In one embodiment, the one or more biosurfactants are present in the composition in critical micelle concentration (CMC).

Advantageously, the biosurfactants according to the present invention are capable of one or more of the following: killing pathogenic agents in/on the skin, modulating the skin's immune system, killing melanocytes to allow for replacement cells to grow, reducing oxidative stress, enhancing multiplication and function of keratinocytes and fibroblasts, and contain components that enhance dermal penetration of the composition. Thus, they provide therapeutic benefits themselves, and can also enhance the effectiveness of other components that may be present in the topical composition in treating skin conditions related to wounds, such as burns, and/or scarring, as well as rejuvenating aging and/or damaged skin.

In one embodiment, the biosurfactants are selected from mannosylerythritol lipids (MEL) and sophorolipids (SLP), which are both glycolipid biosurfactants produced by certain yeasts.

MEL comprise either 4-O-B-D-mannopyranosyl-meso-erythritol or 1-O-B-D-mannopyranosyl-meso-erythritol as the hydrophilic moiety, and fatty acid groups and/or acetyl groups as the hydrophobic moiety. One or two of the hydroxyls, typically at the C4 and/or C6 of the mannose residue, can be acetylated. Furthermore, there can be one to three esterified fatty acids, from 8 to 12 carbons or more in chain length.

MEL and MEL-like substances (e.g., mannose-based substances) are produced mainly by *Pseudozyma* spp. and *Ustilago* spp., with significant variability among MEL structures produced by each species. Certain mannose-based substances having similar properties to MEL can also be produced by *Meyerozyma guilliermondii* yeasts.

MEL are non-toxic and are stable at wide temperatures and pH ranges. Furthermore, MEL can be used without any additional preservatives MEL can be produced in more than 93 different combinations that fall under 5 main categories: MEL A, MEL B, MEL D, Tri-acetylated MEL A, and Tri-acetylated MEL B/C. These molecules can be modified, either synthetically or in nature. For example, MEL can comprise different carbon-length chains or different numbers of acetyl and/or fatty acid groups.

MEL molecules and/or modified forms thereof according to the subject invention can include, for example, tri-acylated, di-acylated, mono-acylated, tri-acetylated, di-acetylated, mono-acetylated and non-acetylated MEL, as well as stereoisomers and/or constitutional isomers thereof.

Other mannose-based substances/MEL-like substances that exhibit similar structures and similar properties, can also be used according to the subject invention, e.g., mannosyl-mannitol lipids (MML), mannosyl-arabitol lipids (MAL), and/or mannosyl-ribitol lipids (MRL).

In preferred embodiments, the concentration of MEL (or MEL-like substances) in the topical cosmetic composition is from 0.001% to 90% of the total composition by weight, from 0.01% to 50%, from 0.05% to 10%, or from 0.1% to 2.0%.

Another useful class of glycolipid according to the subject invention is SLP. *Starmerella* clade yeasts, including *Candida apicola* and *Starmerella bombicola* are two major producers of SLP. SLP consist of a disaccharide sophorose linked to long chain hydroxy fatty acids. These SLPs are a partially acetylated 2-O-β-D-glucopyranosyl-D-glucopyranose unit attached β-glycosidically to 17-L-hydroxyoctadecanoic or 17-L-hydroxy-Δ9-octadecenoic acid. The hydroxy fatty acid is generally 16 or 18 carbon atoms, and may contain one or more unsaturated bonds. The fatty acid carboxyl group can be free (acidic or open form) or internally esterified at the 4''-position (lactone form).

SLP have environmental compatibility, high biodegradability, low toxicity, high selectivity and specific activity in a broad range of temperature, pH and salinity conditions.

In preferred embodiments, SLP concentration in the topical cosmetic composition is from 0.001% to 90% of the total composition by weight, from 0.01% to 50%, from 0.05% to 10%, or from 0.1% to 2.0%. In one embodiment, the topical composition comprises SLP in acidic form.

In a specific preferred embodiment, the topical composition of the subject invention comprises from about 0.1% to 2.0% by weight MEL, preferably about 1.0%; and further comprises from about 0.01% to about 1.0% by weight SLP, preferably about 0.5%.

In one embodiment, the topical composition further comprises cardiolipins (CL). CL are phospholipid biosurfactants, also known by the names 1,3-bis(sn-3'-phosphatidyl)-sn-glycerol, diphosphatidylglycerol lipid, glycerophospholipid or Calcutta antigen. The name "cardiolipin" is derived from where it was first discovered—in the cells of animal hearts. Cardiolipin (CL) makes up about 20% of the total lipid composition of the inner mitochondrial membrane of animal cells, as well as many plant cells. It can be also be found in membranes of some prokaryotic organisms. For example, most bacterial membranes contain CL, as well as some yeasts and fungi (e.g., *Saccharomyces cerevisiae* and *Aspergillus fumigatus*).

As skin cells age, CL content in the mitochondria decreases due to the accumulation of poly-unsaturated fatty acids that weaken the molecules against oxidative damage. An increase in CL levels, however, restores skin cells to their youthful function and appearance.

CL molecules comprise two phosphatidic acid moieties connected by a glycerol at the center, as well as four distinct acyl groups with fatty acid residues attached thereto. Because of the four acyl groups, CL species can vary widely in terms of the type and/or types of fatty acids that make up their tails. In general, the head group of cardiolipin and certain amino acid residues interact strongly via electrostatic forces, hydrogen bonds, and water molecules to facilitate, for example, conformational changes to proteins to modulate their structures and functions. The acyl chains, on the other hand, retain their flexibility and interact through van der Waals forces with various proteins and surfaces. Additionally, CL may modulate the activity of some membrane proteins by forming clusters and non-bilayer structures. (Christie 2018).

In preferred embodiments, CL concentration in the topical cosmetic composition is from 0.001% to 90% of the total composition by weight, from 0.01% to 50%, from 0.05% to 10%, or from 0.1% to 2.0%.

In one embodiment, a combination of SLP, MEL and CL are utilized in the composition, wherein the SLP and MEL serve as, for example, healing agents, and the CL serve as, for example, skin rejuvenating agents.

In one embodiment, the biosurfactants can comprise one or more lipopeptides, such as, for example, surfactin, iturin, fengycin, arthrofactin, viscosin, amphisin, syringomycin, and/or lichenysin.

In a specific embodiment, the lipopeptide biosurfactant is surfactin. Lipopeptides are produced by a variety of probiotics and non-pathogenic bacteria, such as, e.g., *Bacillus natto, Bacillus coagulans, Bacillus subtilis, Bacillus amyloliquefaciens*, lactic acid bacteria, and others.

In one embodiment, the surfactants can comprise one or more microbial-produced fatty acid ester compounds and/or fatty acid ether compounds having physical properties and/or behaviors similar to those of biosurfactants, but which are not commonly known as biosurfactants.

In certain embodiments, the fatty acid ester compounds can include, for example, highly esterified oleic fatty acids, such as oleic fatty acid ethyl esters and/or oleic fatty acid methyl esters (FAME).

In some embodiments, the topical composition can comprise these other amphiphilic molecules at concentrations of about 0.001% to 90% of the total composition by weight, about 0.01% to 50%, about 0.05% to 10%, about 0.1% to 5.0%, or about 0.01% to 2.0%.

In some embodiments, the amphiphilic molecules are utilized in a crude form, wherein the molecule is present in the growth medium (e.g., broth) in which a amphiphile-producing microorganism is cultivated and is collected therefrom without purification. The crude form can comprise, for example, at least 0.001%, 1%, 5%, 10%, 20%, 30%, 40%, 50%, 60%, 70%, 80%, 90% or 99% amphiphilic molecules in the growth medium. In alternate embodiments, the amphiphilic molecules are purified from the products of cultivation.

In some embodiments, the composition comprises live or inactivated microorganisms capable of producing growth by-products useful for skin healing and rejuvenation (e.g., biosurfactants). In certain embodiments, the microorganisms are yeasts, such as, e.g., *Starmerella bombicola, Wickerhamoinyces anomalus, Meyerozyma (Pichia) guilliermondii*, and/or *Pseudozyma aphidis*. In one specific embodiment, the composition comprises live or inactivated *Wickerhamomyces anomalus*.

Additional microbial growth by-products useful according to the present invention include mannoprotein, beta-glucan, enzymes, and other metabolites that have bio-emulsifying and surface/interfacial tension-reducing properties.

In some embodiments, the topical cosmetic composition can comprise therapeutically effective amounts of enzymes and/or proteins produced by microorganisms. For example, from about 0.001% to about 20% by weight, about 0.01% to about 15% by weight, or about 0.05% to about 10% by weight, of one or more enzymes and/or proteins can be included. These can include, but are not limited to, exo-beta-1,3-glucanase; chitinase; esterases; lipases; glycosidases; amylases; and proteases beneficial for improving skin health.

In some embodiments, the topical therapeutic composition can further comprise a dermatologically-acceptable carrier or vehicle.

The carrier or vehicle may include, for example, water; saline; physiological saline; ointments; creams; oil-water emulsions; water-in-oil emulsions; silicone-in-water emulsions; water-in-silicone emulsions; wax-in-water emulsions; water-oil-water triple emulsions; microemulsions; gels; vegetable oils; mineral oils; ester oils such as octal palmitate, isopropyl myristate and isopropyl palmitate; ethers such as dicapryl ether and dimethyl isosorbide; alcohols such as ethanol and isopropanol; fatty alcohols such as cetyl alcohol, cetearyl alcohol, stearyl alcohol and behenyl alcohol; isoparaffins such as isooctane, isododecane (IDD) and isohexadecane; silicone oils such as cyclomethicone, dimethicone, dimethicone cross-polymer, polysiloxanes and their derivatives, preferably organomodified derivatives including PDMS, dimethicone copolyol, dimethiconols, and amodimethiconols; hydrocarbon oils such as mineral oil, petrolatum, isoeicosane and polyolefins, e.g., (hydrogenated) polyisobutene; polyols such as propylene glycol, glycerin, butylene glycol, pentylene glycol, hexylene glycol, caprylyl glycol; waxes such as beeswax, carnauba, ozokerite, microcrystalline wax, polyethylene wax, and botanical waxes; or any combinations or mixtures of the foregoing. Aqueous vehicles may include one or more solvents miscible with water, including lower alcohols, such as ethanol, isopropanol, and the like. The vehicle may comprise from about 1% to about 99% by weight of the composition, from 10% to about 85%, from 25% to 75%, or from 50% to about 65%.

As used herein, the term "oil" includes silicone oils unless otherwise indicated. The emulsion may include an emulsifier, such as a nonionic, anionic or amphoteric surfactant, or a gallant, typically in an amount from about 0.001% to about 5% by weight.

In some embodiments, the topical composition can further comprise a topical or local anesthetic. Topical anesthetics can include, for example, Tetracaine, Benzocaine, Proparacaine, Procaine, Propoxycaine, Dibucaine, Lidocaine, Dyclonine and Promazine. The anesthetic may be present in varying concentrations, for example, between about 0.05% and 25% by weight, between about 0.25% and 10% by weight, between about 0.5% and 10% by weight, and between about 1% and 5% by weight. The exact dose of anesthetic to be employed in a given formulation will depend on a number of factors such as the particular anesthetic to be employed. For example, in compositions containing lidocaine, an exemplary preferred dose range is between approximately 1% and 20% by weight and in compositions containing tetracaine an exemplary preferred dose is approximately 0.5%.

In some embodiments, the topical composition can further comprise additional adjuvants and additives commonly included in skin care compositions, such as, for example, organic solvents, stabilizers, silicones, thickeners, softeners, sunscreens, moisturizers, fragrances or others described herein. The amounts of each ingredient, whether active or inactive, are those conventionally used in the cosmetic field to achieve their intended purpose, and typically range from about 0.0001% to about 25%, or from about 0.001% to about 20% of the composition, although the amounts may fall outside of these ranges. The nature of these ingredients and their amounts must be compatible with the production and function of the compositions of the disclosure.

In one embodiment, the composition may include additional skin actives, including but not limited to, keratolytic agents, desquamating agents, keratinocyte proliferation enhancers, collagenase inhibitors, elastase inhibitors, depigmenting agents, anti-inflammatory agents, steroids, anti-acne agents, antioxidants, and advanced glycation end-product (AGE) inhibitors, to name only a few.

In one embodiment, the composition may include anti-aging components, including, but not limited to, botanicals (e.g., *Butea frondosa* extract); phytol; phytonic acid; phospholipids; silicones; petrolatum; triglycerides; omega fatty acids; retinoids; hydroxy acids (including alpha-hydroxy acids and beta-hydroxy acids), salicylic acid and alkyl salicylates; exfoliating agents (e.g., glycolic acid, 3,6,9-trioxaundecanedioic acid, etc.), estrogen synthetase stimulating compounds (e.g., caffeine and derivatives); compounds capable of inhibiting 5 alpha-reductase activity (e.g., linolenic acid, linoleic acid, finasteride, and mixtures thereof); and barrier function enhancing agents (e.g., ceramides, glycerides, cholesterol and its esters, alpha-hydroxy and omega-hydroxy fatty acids and esters thereof.)

Exemplary retinoids include, without limitation, retinoic acid (e.g., all-trans, or 9-cis, or 13-cis), and derivatives thereof, retinaldehyde, retinol (Vitamin A) and esters thereof, such as retinyl palmitate, retinyl acetate and retinyl propionate, and salts thereof. When present, the retinoids will typically be included in amounts from about 0.0001% to about 5% by weight, more typically from about 0.01% to about 2.5% by weight, or from about 0.1% to about 1.0% by weight.

In one embodiment, the composition may include an exfoliating agent. Suitable exfoliating agents include, for example, alpha-hydroxy acids, beta-hydroxy acids, oxaacids, oxadiacids, and their derivatives, such as esters, anhydrides and salts thereof. Suitable hydroxy acids include, for example, glycolic acid, lactic acid, malic acid, tartaric acid, citric acid, 2-hydroxyalkanoic acid, mandelic acid, salicylic acid and derivatives thereof. One exemplary exfoliating agent is glycolic acid. When present, the exfoliating agent may comprise from about 0.001% to about 20% by weight of the composition.

In one embodiment, the composition may comprise one or more antioxidants. Suitable antioxidants include, for example, compounds having phenolic hydroxy functions, such as ascorbic acid and its derivatives/esters; beta-carotene; catechins; curcumin; ferulic acid derivatives (e.g., ethyl ferulate, sodium ferulate); gallic acid derivatives (e.g., propyl gallate); lycopene; reductic acid; rosmarinic acid; tannic acid; tetrahydrocurcumin; tocopherol and its derivatives, including tocopheryl acetate; uric acid; or any mixtures thereof. Other suitable antioxidants are those that have one or more thiol functions (—SH), in either reduced or non-reduced form, such as glutathione, lipoic acid, thioglycolic acid, and other sulfhydryl compounds. The antioxidant may be inorganic, such as bisulfites, metabisulfites, sulfites, or other inorganic salts and acids containing sulfur. Antioxidants may comprise, individually or collectively, from about 0.001% to about 10% (w/w), or from about 0.01% to about 5% (w/w) of the total weight of the composition.

Non-biological surfactants can also be added to the formulation. Examples of surfactants include, but are not limited to, alkyl sulfates, alkyl ether sulfates (e.g., sodium/ammonium lauryl sulfates and sodium/ammonium laureth sulfates), amphoterics (e.g., amphoacetates and amphopropionates), sulfosuccinates, alkyl polyglucosides, betaines (e.g., cocamidopropul betaine (CAPB)), sultaines, sacrosinates, isethionates, taurates, ethoxylated sorbitan esters, alkanolamides and amino-acid based surfactants.

Viscosity modifiers can also be added to the compositions, including, for example, cocamide DEA, oleamide DEA, sodium chloride, cellulosic polymers, polyacrylates, ethoxylated esters, alcohol, glycols, xylene sulfonates, polysorbate 20, alkanolamides, and cellulose derivatives (e.g., hydroxypropyl methylcellulose and hydroxyethyl cellulose).

Polymers can also be added, including, for example, xanthan gum, guar gum, polyquaternium-10, PEG-120 methyl glucose dioleate, PEG-150 distearate, PEG-150 polyglyceryl-2 tristearate and PEG-150 pentaerythrityl tetrastearate A sunscreen or combination of sunscreens may be included to protect the skin from both UVA and UVB rays. Among the sunscreens that can be employed in the present compositions are avobenzone, cinnamic acid derivatives (such as octylmethoxy cinnamate), octyl salicylate, oxybenzone, octocrylene, titanium dioxide, zinc oxide, or any mixtures thereof. The sunscreen may be present from about 1 wt % to about 30 wt % of the total weight of the composition.

The composition may optionally comprise other components, additives or adjuvants known to those skilled in the art including, but not limited to: skin penetration enhancers; emollients (e.g., isopropyl myristate, petrolatum, volatile or non-volatile silicones oils, such as methicone and dimethicone, ester oils, mineral oils, and fatty acid esters); humectants (e.g., glycerin, hexylene glycol, caprylyl glycol); skin plumpers (e.g., palmitoyl oligopeptide, collagen, collagen and/or glycosaminoglycan (GAG) enhancing agents); anti-inflammatory agents (e.g., Aloe vera, bioflavonoids, diclofenac, salicylic acid); chelating agents (e.g., EDTA or a salt thereof, such as disodium EDTA); vitamins (e.g., tocopherol and ascorbic acid); vitamin derivatives (e.g., ascorbyl monopalmitate, tocopheryl acetate, Vitamin E palmitate); thickeners (e.g., hydroxyalkyl cellulose, carboxymethylcellulose, carbombers, and vegetable gums, such as xanthan gum); gelling agents (e.g., ester-terminated polyester amides); structuring agents; proteins (e.g., lactoferrin); immune modulators (e.g., corticosteroids and non-steroidal immune modulators).

Other components that may be included are film formers, moisturizers, minerals, viscosity and/or rheology modifiers, insect repellents, skin cooling compounds, skin protectants, lubricants, preservatives, pearls, chromalites, micas, conditioners, anti-allergenics, antimicrobials (e.g., antifungals, antivirals, antibacterials), antiseptics, pharmaceutical agents, photostabilizing agents, surface smoothers, optical diffusers, and exfoliation promoters. Details with respect to these and other suitable cosmetic ingredients can be found in the "International Cosmetic Ingredient Dictionary and Handbook," 10th Edition (2004), published by the Cosmetic, Toiletry, and Fragrance Association (CTFA), at pp. 2177-2299, which is herein incorporated by reference in its entirety. The amounts of these various substances are those that are conventionally used in the cosmetic or pharmaceutical fields, for example, they can constitute from about 0.01% to about 20% of the total weight of the composition.

The composition can include pH adjusters (e.g., citric acid, ethanolamine, sodium hydroxide, etc.) to be formulated within a wide range of pH levels. In one embodiment, the pH of the topical composition ranges from 1.0 to 13.0. In some embodiments, the pH of the topical composition ranges from 2.0 to 12.0. Other pH ranges suitable for the subject composition include from 3.5 to 7.0, or from 7.0 to 10.5. Suitable pH adjusters such as sodium hydroxide, citric acid and triethanolamine may be added to bring the pH within the desired range.

The composition may be formulated as a suspension, emulsion, hydrogel, multiphase solution, vesicular dispersion or in any other known form of topical skin composition.

In certain embodiments, the topical composition may be formulated so that it can be applied, for example, via pen, tube, bottle, brush, stick, sponge, cotton swab, towelette (wipe), sprayer, dropper, hand or finger.

The composition may be formulated in a variety of product forms, such as, for example, a lotion, cream, serum, spray, aerosol, liquid cake, ointment, essence, gel, paste, patch, pencil, powder, towelette, soap, shampoo, conditioner, stick, foam, mousse, elixir or concentrate. In preferred embodiments, the composition is formulated so that is particularly suitable for topical administration to the skin.

In one embodiment, the composition can be incorporated into a wound dressing or bandage that may be applied, attached or coupled to one or more layers of the skin or tissue of the subject. For example, the composition may be applied to a wound dressing, which can then be placed over the area of skin being treated.

Wound dressings can be made, for example, from any material that is dermatologically-acceptable and suitable for placing on a wound. In exemplary embodiments, the wound dressing may be made from a woven or non-woven fabric of synthetic or non-synthetic fibers, or any combination thereof. The dressing may also include a support, such as a polymer foam, a natural or man-made sponge, a gel or a membrane that may absorb or have disposed thereon, a composition. Again by way of example, the support can be a film, a natural or synthetic polymer, or a rigid or malleable material (e.g., gauze). The wound dressing may be absorbent and can be, for example, wetted with a composition of the present invention before applying the gauze to a wound, scar or other site.

In one embodiment, the wound dressing is fashioned out of the polymer polyhydroxybutyrate (PHB). PHB is a biodegradable polyester produced by bacteria. The compound can be fashioned into a flexible, breathable matrix, which, when impregnated with a composition of the subject invention, provides a gradual release of healing and rejuvenating compounds to the underlying skin.

In one embodiment, the wound dressing may be impregnated with a composition of the subject invention and, optionally, dried. This allows the impregnated dressing to be stored for later use, or to avoid excessively dampening an injured area. The composition may be applied to a surface of the dressing by wetting the surface with a solution of the composition and drying the dressing to deposit the composition thereon.

Methods of Promoting Wound and Scar Healing

In certain embodiments, the subject invention provides methods to promote the healing of a skin condition, wherein a topical therapeutic microbe-based composition of the subject invention is applied directly to an area of the skin where such a condition exists. In preferred embodiments, the skin condition is a wound, such as a burn, or a scar. The composition can be applied to any external area of skin, including, for example, the skin of the face, ears, scalp, neck, back, shoulders, arms, hands, fingers, chest, torso, abdomen, underarms, feet, toes, buttocks, and legs.

In some embodiments, "applying" the composition can comprise leaving the composition on the area of skin, and/or rubbing it in so that the composition is absorbed into the area completely. In some embodiments, the composition can be applied to the skin for a therapeutically-effective amount of time and then rinsed or removed from the skin using, for example, water or a cloth.

In yet another embodiment, the composition can be impregnated into a wound dressing and applied to the skin by covering the wound with the impregnated dressing according to standard dressing procedures. In a specific embodiment, the wound dressing is made out of PHB.

In certain embodiments, the topical composition is applied from zero to ten times daily, preferably at least once per day or at least once every other day. In some embodiments, the topical composition is applied daily or every other day for an indefinite period of time, e.g., for at least one, two, three weeks, or longer, in order to achieve and/or maintain the treatment of the skin condition.

Preferably, when applied to a wound, the wound has entered the proliferative phase of healing or a phase of healing thereafter. In some embodiments, determination of which phase of healing the wound has entered can be determined visually, or using standard assays or tests for making such determinations.

In one embodiment, the composition can be applied to the skin in liberal amounts, preferably to cover the entire area desired to be treated; however, only a thin coating should be needed to achieve a desired effect. In one embodiment, the composition is applied in an amount from about 0.001 to about 100 mg per $cm^2$ of skin, more typically from about 0.01 to about 20 mg/$cm^2$, or from about 0.1 to about 10 mg/$cm^2$. More or less may be used, however, depending upon the size of the area of skin to be treated.

In preferred embodiments, the method comprises applying one or more microbial growth by-products, and optionally, a topically-acceptable carrier, to the area of skin. In certain embodiments, microbial growth by-products are amphiphilic molecules, such as biosurfactants selected from, for example, low molecular weight glycolipids (e.g., sophorolipids, rhamnolipids, cellobiose lipids, mannosylerythritol lipids and trehalose lipids), lipopeptides (e.g., surfactin, iturin, fengycin, arthrofactin and lichenysin), flavolipids, phospholipids (e.g., cardiolipins), fatty acid ester compounds, fatty acid ether compounds, and high molecular weight polymers such as lipoproteins, lipopolysaccharide-protein complexes, and polysaccharide-protein-fatty acid complexes.

In additional embodiments, the composition comprises therapeutically effective amounts of enzymes and/or proteins produced by microorganisms, such as, e.g., exo-beta-1,3-glucanase; chitinase; esterases; lipases; glycosidases; amylases; and proteases beneficial for improving skin health. In some embodiments, the composition comprises mannoprotein and/or beta-glucan, which are bioemulsifiers present as part of yeast cell walls.

In one embodiment, the method further comprises applying one or more microorganisms to the area of skin, wherein the microorganisms are capable of producing useful metabolites, such as amphiphiles, enzymes and/or proteins. The microorganisms can be, for example, live or inactivated yeasts, such as, for example, S. bombicola, M. guilliermondii, W. anomalus, and/or P. aphidis. Preferably, in one embodiment, the yeast is live or inactive W. anomalus.

Other ingredients that are helpful for improving skin health can be applied to the skin along with various embodiments of the topical therapeutic microbe-based composition, depending upon the skin condition being treated.

The topical compositions and methods of the subject invention can be used to promote the healing of wounds categorized as open wounds, including burns and burn-related irritation, blisters and rashes. Preferably, the wound has passed the inflammatory phase of healing and has entered the proliferative phase of healing or a later phase of healing.

Additionally, the topical compositions and methods of the subject invention can be used to promote the healing of scars (e.g., hypertrophic scars, acne scars, contractures and/or keloids). For example, the subject invention can be used to ameliorate or reduce the appearance and/or presence of a scar, or ameliorate or reduce the negative effects of a scar, such as immobility, pain or itching.

Growth of Microbes and Production of Microbial Growth By-Products

The subject invention provides methods for cultivating microorganisms and production of microbial metabolites and/or other by-products of microbial growth. As used herein "fermentation" refers to growth of cells under controlled conditions. The growth could be aerobic or anaerobic.

In one embodiment, the subject invention provides materials and methods for the production of biomass (e.g., viable cellular material), extracellular metabolites (e.g. small molecules and excreted proteins), residual nutrients and/or intracellular components (e.g. enzymes and other proteins).

The microbe growth vessel used according to the subject invention can be any fermenter or cultivation reactor for industrial use. In one embodiment, the vessel may have functional controls/sensors or may be connected to functional controls/sensors to measure important factors in the cultivation process, such as pH, oxygen, pressure, temperature, agitator shaft power, humidity, viscosity and/or microbial density and/or metabolite concentration.

In a further embodiment, the vessel may also be able to monitor the growth of microorganisms inside the vessel (e.g., measurement of cell number and growth phases). Alternatively, a daily sample may be taken from the vessel and subjected to enumeration by techniques known in the art, such as dilution plating technique.

In one embodiment, the method includes supplementing the cultivation with a nitrogen source. The nitrogen source can be, for example, potassium nitrate, ammonium nitrate ammonium sulfate, ammonium phosphate, ammonia, urea, and/or ammonium chloride. These nitrogen sources may be used independently or in a combination of two or more.

The method can provide oxygenation to the growing culture. One embodiment utilizes slow motion of air to remove low-oxygen containing air and introduce oxygenated air. The oxygenated air may be ambient air supplemented daily through mechanisms including impellers for mechanical agitation of the liquid, and air spargers for supplying bubbles of gas to the liquid for dissolution of oxygen into the liquid.

The method can further comprise supplementing the cultivation with a carbon source. The carbon source is typically a carbohydrate, such as glucose, sucrose, lactose, fructose, trehalose, mannose, mannitol, and/or maltose; organic acids such as acetic acid, fumaric acid, citric acid, propionic acid, malic acid, malonic acid, and/or pyruvic acid; alcohols such as ethanol, propanol, butanol, pentanol, hexanol, isobutanol, and/or glycerol; fats and oils such as soybean oil, rice bran oil, olive oil, corn oil, sesame oil, and/or linseed oil; etc. These carbon sources may be used independently or in a combination of two or more.

In one embodiment, growth factors and trace nutrients for microorganisms are included in the medium. This is particularly preferred when growing microbes that are incapable of producing all of the vitamins they require. Inorganic nutrients, including trace elements such as iron, zinc, copper, manganese, molybdenum and/or cobalt may also be included in the medium. Furthermore, sources of vitamins, essential amino acids, and microelements can be included, for example, in the form of flours or meals, such as corn flour, or in the form of extracts, such as yeast extract, potato extract, beef extract, soybean extract, banana peel extract, and the like, or in purified forms. Amino acids such as, for example, those useful for biosynthesis of proteins, can also be included.

In one embodiment, inorganic salts may also be included. Usable inorganic salts can be potassium dihydrogen phosphate, dipotassium hydrogen phosphate, disodium hydrogen phosphate, magnesium sulfate, magnesium chloride, iron sulfate, iron chloride, manganese sulfate, manganese chloride, zinc sulfate, lead chloride, copper sulfate, calcium chloride, calcium carbonate, and/or sodium carbonate. These inorganic salts may be used independently or in a combination of two or more.

In some embodiments, the method for cultivation may further comprise adding additional acids and/or antimicrobials in the liquid medium before and/or during the cultivation process. Antimicrobial agents or antibiotics are used for protecting the culture against contamination. Additionally, antifoaming agents may also be added to prevent the formation and/or accumulation of foam during cultivation.

The pH of the mixture should be suitable for the microorganism of interest. Buffers, and pH regulators, such as carbonates and phosphates, may be used to stabilize pH near a preferred value. When metal ions are present in high concentrations, use of a chelating agent in the liquid medium may be necessary.

The method and equipment for cultivation of microorganisms and production of the microbial by-products can be performed in a batch, quasi-continuous, or continuous processes.

In one embodiment, the method for cultivation of microorganisms is carried out at about 5° to about 100° C., preferably, 15 to 60° C., more preferably, 25 to 50° C. In a further embodiment, the cultivation may be carried out continuously at a constant temperature. In another embodiment, the cultivation may be subject to changing temperatures.

In one embodiment, the equipment used in the method and cultivation process is sterile. The cultivation equipment such as the reactor/vessel may be separated from, but connected to, a sterilizing unit, e.g., an autoclave. The cultivation equipment may also have a sterilizing unit that sterilizes in situ before starting the inoculation. Air can be sterilized by methods know in the art. For example, the ambient air can pass through at least one filter before being introduced into the vessel. In other embodiments, the medium may be pasteurized or, optionally, no heat at all added, where the use of low water activity and low pH may be exploited to control bacterial growth.

In one embodiment, the subject invention provides methods of producing a microbial metabolite, including, for example, a biosurfactant, enzyme and/or other protein, by cultivating a microbe strain of the subject invention under conditions appropriate for growth and production of the metabolite. The metabolite content of the resulting culture can be, for example, at least 20%, 30%, 40%, 50%, 60%, 70%, 80%, or 90%.

The biomass content of the fermentation broth may be, for example from 5 g/l to 180 g/l or more, or 10 g/l to 150 g/l.

The microbial growth by-product produced by microorganisms of interest may be retained in the microorganisms or secreted into the liquid medium. In another embodiment, the method for producing microbial growth by-product may further comprise steps of concentrating and purifying the microbial growth by-product of interest. In a further embodiment, the liquid medium may contain compounds that stabilize the activity of microbial growth by-product.

In one embodiment, all of the microbial culture is removed upon the completion of the cultivation (e.g., upon, for example, achieving a desired cell density, or density of a specified metabolite in the medium). In this batch procedure, an entirely new batch is initiated upon harvesting of the first batch.

In another embodiment, only a portion of the fermentation product is removed at any one time. In this embodiment, biomass with viable cells remains in the vessel as an inoculant for a new cultivation batch. The composition that is removed can be a cell-free broth or contain cells. In this manner, a quasi-continuous system is created.

Advantageously, the method does not require complicated equipment or high energy consumption. The microorganisms of interest can be cultivated at small or large scale on site and utilized, even being still-mixed with their media. Similarly, the microbial metabolites can also be produced at large quantities at the site of need.

The microorganisms can be, for example, bacteria, yeast and/or fungi. These microorganisms may be natural, or genetically modified microorganisms. For example, the microorganisms may be transformed with specific genes to exhibit specific characteristics. The microorganisms may also be mutants of a desired strain. As used herein, "mutant" means a strain, genetic variant or subtype of a reference microorganism, wherein the mutant has one or more genetic variations (e.g., a point mutation, missense mutation, nonsense mutation, deletion, duplication, frameshift mutation or repeat expansion) as compared to the reference microorganism. Procedures for making mutants are well known in the microbiological art. For example, UV mutagenesis and nitrosoguanidine are used extensively toward this end.

In certain embodiments, the microbes are capable of producing amphiphilic molecules, enzymes, proteins and/or biopolymers. Microbial biosurfactants, in particular, are produced by a variety of microorganisms such as bacteria, fungi, and yeasts, including, for example, *Agrobacterium* spp. (e.g., *A. radiobacter*); *Arthrobacter* spp.; *Aspergillus* spp.; *Aureobasidium* spp. (e.g., *A. pullulans*); *Azotobacter* (e.g., *A. vinelandii*, *A. chroococcum*); *Azospirillum* spp. (e.g., *A. brasiliensis*); *Bacillus* spp. (e.g., *B. subtilis, B. amyloliquefaciens, B. pumillus, B. cereus, B. licheniformis, B. firmus, B. laterosporus, B. megaterium*); *Blakeslea*; *Candida* spp. (e.g., *C. albicans, C. rugosa, C. tropicalis, C. lipolytica, C. torulopsis*); *Clostridium* (e.g., *C. butyricum, C. tyrobutyricum, C. acetobutyricum*, and *C. beijerinckii*); *Campylobacter* spp.; *Cornybacterium* spp.; *Cryptococcus* spp.; *Debaryomyces* spp. (e.g., *D. hansenii*); *Entomophthora* spp.; *Flavobacterium* spp.; *Gordonia* spp.; *Hansenula* spp.; *Hanseniaspora* spp. (e.g., *H. uvarum*); *Issatchenkia* spp; *Kluyveromyces* spp.; *Meyerozyma* spp. (e.g., *M. guilliermondii*); *Mortierella* spp.; *Mycorrhiza* spp.; *Mycobacterium* spp.; *Nocardia* spp.; *Pichia* spp. (e.g., *P. anomala, P. guilliermondii, P. occidentalis, P. kudriavzevii*); *Phycomyces* spp.; *Phythium* spp.; *Pseudomonas* spp. (e.g., *P. aeruginosa, P. chlororaphis, P. putida, P. florescens, P. Tragi, P. syringae*); *Pseudozyma* spp. (e.g., *P. aphidis*); *Ralslonia* spp. (e.g., *R. eulropha*); *Rhodococcus* spp. (e.g., *R. erythropolis*); *Rhodospirillum* spp. (e.g., *R. rubrum*); *Rhizobium* spp.;

*Rhizopus* spp.; *Saccharomyces* spp. (e.g., *S. cerevisiae, S. boulardii sequela, S. torula*); *Sphingomonas* spp. (e.g., *S. paucimobilis*); *Starmerella* spp. (e.g., *S. bombicola*); *Thraustochytrium* spp.; *Torulopsis* spp.; *Ustilago* spp. (e.g., *U. maydis*); *Wickerhamomyces* spp. (e.g., *W. anomalus*); *Williopsis* spp.; and/or *Zygosaccharomyces* spp. (e.g., *Z. bailii*).

In one embodiment, the method utilizes a yeast, such as, for example, *Wickerhamomyces anomalus, Pseudozyma aphidis, Starmerella bombicola, Pichia kudriavzevii* or *Pichia guilliermondii (Meyerozyma guilliermondii)*. These yeasts are effective producers of various amphiphilic molecules, including glycolipids, enzymes and other useful metabolites. In a specific embodiment, the method utilizes *W. anomalus*.

Other microbial strains including, for example, other strains capable of accumulating significant amounts of, for example, amphiphilic molecules, can be used in accordance with the subject invention. Additional metabolites useful according to the present invention include mannoprotein, beta-glucan and other molecules that have bio-emulsifying and surface/interfacial tension-reducing properties.

Preparation of Microbe-Based Products

One microbe-based product of the subject invention is simply the fermentation broth containing the microorganism and/or the microbial metabolites produced by the microorganism and/or any residual nutrients. The product of fermentation may be used directly without extraction or purification.

However, extraction and purification can be easily achieved using standard extraction and/or purification methods or techniques described in the literature. For example, in certain embodiments, the microbe-based product comprises simply the by-products of microbial growth, either in crude or purified form. In particular embodiments, the by-products are biosurfactants produced by the microorganisms grown according to the subject invention.

The microbes and/or broth resulting from the microbial growth can be removed from the growth vessel and transferred via, for example, piping for immediate use.

In other embodiments, the composition (microbes, broth, or microbes and broth) can be placed in containers of appropriate size, taking into consideration, for example, the intended use, the contemplated method of application, the size of the fermentation tank, and any mode of transportation from microbe growth facility to the location of use. Thus, the containers into which the microbe-based composition is placed may be, for example, from 1 gallon to 1,000 gallons or more. In other embodiments the containers are 2 gallons, 5 gallons, 25 gallons, or larger.

In certain embodiments, the compositions of the subject invention have advantages over, for example, biosurfactants alone, including one or more of the following: high concentrations of mannoprotein as a part of yeast cell wall's outer surface (mannoprotein is a highly effective bioemulsifier capable of reaching up to an 80% emulsification index); the presence of biopolymer beta-glucan (an emulsifier) in yeast cell walls; the presence of biosurfactants in the culture, which are capable of reducing both surface and interfacial tension; and the presence of metabolites (e.g., lactic acid, ethanol, etc.).

Upon harvesting the microbe-based composition from the growth vessels, further components can be added as the harvested product is placed into containers and/or piped (or otherwise transported for use). The additives can be, for example, buffers, carriers, other microbe-based compositions produced at the same or different facility, viscosity modifiers, preservatives, nutrients for microbe growth, tracking agents, solvents, biocides, other microbes and other ingredients specific for an intended use.

Other suitable additives, which may be contained in the formulations according to the invention, include substances that are customarily used for such preparations. Example of such additives include surfactants, emulsifying agents, lubricants, buffering agents, solubility controlling agents, pH adjusting agents, preservatives, stabilizers and ultra-violet light resistant agents.

In one embodiment, the composition may further comprise buffering agents including organic and amino acids or their salts. Suitable buffers include citrate, gluconate, tartarate, malate, acetate, lactate, oxalate, aspartate, malonate, glucoheptonate, pyruvate, galactarate, glucarate, tartronate, glutamate, glycine, lysine, glutamine, methionine, cysteine, arginine and a mixture thereof. Phosphoric and phosphorous acids or their salts may also be used. Synthetic buffers are suitable to be used but it is preferable to use natural buffers such as organic and amino acids or their salts listed above.

In a further embodiment, pH adjusting agents include potassium hydroxide, ammonium hydroxide, potassium carbonate or bicarbonate, hydrochloric acid, nitric acid, sulfuric acid or a mixture thereof.

In one embodiment, additional components such as an aqueous preparation of a salt, such as sodium bicarbonate or carbonate, sodium sulfate, sodium phosphate, sodium biphosphate, can be included in the formulation.

Advantageously, in accordance with the subject invention, the microbe-based product may comprise the medium in which the microbes were grown. The product may be, for example, at least, by weight, 1%, 5%, 10%, 25%, 50%, 75%, or 100% growth medium. The amount of biomass in the product, by weight, may be, for example, anywhere from 0% to 100% inclusive of all percentages therebetween.

Optionally, the product can be stored prior to use. The storage time is preferably short. Thus, the storage time may be less than 60 days, 45 days, 30 days, 20 days, 15 days, 10 days, 7 days, 5 days, 3 days, 2 days, 1 day, or 12 hours. In a preferred embodiment, if live cells are present in the product, the product is stored at a cool temperature such as, for example, less than 20° C., 15° C., 10° C., or 5° C. On the other hand, a biosurfactant composition can typically be stored at ambient temperatures.

EXAMPLES

A greater understanding of the present invention and of its many advantages may be had from the following examples, given by way of illustration. The following examples are illustrative of some of the methods, applications, embodiments and variants of the present invention. They are not to be considered as limiting the invention. Numerous changes and modifications can be made with respect to the invention.

Example 1—Burn Healing

A subject received an alkaline burn on the hand due to exposure to sodium hydroxide. The burn had entered the proliferative phase of healing. A composition comprising MEL (about 1.0% by weight), SLP (about 0.5% by weight), and Aloe vera gel was applied to the site of the burn once daily. Within one week, the burn had healed completely, and with no visible scarring.

Example 2—Scar Healing

In certain embodiments, the subject compositions and methods can be used for reducing the appearance of dermal scars, for example, scars resulting from injury, acne, or surgery, including plastic/reconstructive surgery.

In one embodiment, a method is provided for reducing the appearance of a scar by applying a topical composition of the subject invention to the scar, wherein the composition comprises MEL and SLP, and/or other agents for skin health. In one embodiment, the composition can be formulated as a gel or a cream. In preferred embodiments, the composition further comprises Aloe vera extract, for example, in gel form.

In one embodiment the amount of MEL in the composition is from about 0.1% to 2.0% by weight, preferably about 1.0%. In one embodiment, the amount of SLP in the composition is from about 0.01% to about 1.0% by weight, preferably about 0.5%.

Advantageously, in one embodiment, the subject compositions can help to realign the misaligned collagen matrix that forms a dermal scar, as well as inhibit the number of myofibroblasts present in the dermis in order to diminish the appearance of the scar.

REFERENCES

Christie, W. W., "Cardiolipin (Diphosphatidylglycerol)", The LipidWeb, updated Oct. 15, 2018, http://www.lipidhome.co.uk/lipids/complex/dpg/index.htm. ("Christie 2018").

Rowan, M. P., et al. (2015). Burn wound healing and treatment: review and advancements. Critical Care. 12 Jun. 2015. doi: 10.1186/s13054-015-0961-2. ("Rowan et al. 2015").

Tiwari, V. K. (2012). Burn wound: How it differs from other wounds? Indian J Plast Surg. 2012 May-August; 45(2): 364-373. doi: 10.4103/0970-0358.101319. ("Tiwari 2012").

We claim:

1. A topical therapeutic composition for treating and/or preventing a skin condition, the composition comprising a therapeutically-effective amount of a sophorolipid (SLP) biosurfactant, a mannosylerythritol lipid (MEL) biosurfactant, cellular components of *Starmerella bombicola*, cellular components of *Pseudozyma aphidis*, lactoferrin and a dermatologically-acceptable carrier.

2. The composition of claim 1, further comprising one or more skin active substances selected from anesthetics, keratolytic agents, desquamating agents, keratinocyte proliferation enhancers, collagenase inhibitors, elastase inhibitors, depigmenting agents, anti-inflammatory agents, steroids, anti-acne agents, and advanced glycation end-product (AGE) inhibitors.

3. The composition of claim 1, further comprising Aloe vera extract.

4. A wound dressing comprising a dermatologically-acceptable dressing material that has been impregnated with a composition comprising a therapeutically-effective amount of a SLP biosurfactant, a MEL biosurfactant, lactoferrin, and, optionally, dried for storage, cellular components of *Starmerella bombicola*, and cellular components of *Pseudozyma aphidis*.

5. A method for promoting the healing of a skin condition, wherein said method comprises applying a composition comprising a therapeutically-effective amount of a SLP biosurfactant, a MEL biosurfactant, lactoferrin and a dermatologically-acceptable carrier to an area of the subject's skin where such a condition exists, cellular components of *Starmerella bombicola*, and cellular components of *Pseudozyma aphidis*.

6. The method of claim 5, which further comprises applying Aloe vera gel to said area of the subject's skin.

7. The method of claim 5, wherein the skin condition is a wound or a scar.

8. The method of claim 7, wherein the wound is a burn.

9. The method of claim 7, used to prevent a wound from scarring.

10. The method of claim 7, used to reduce the appearance of a scar.

11. The method of claim 5, comprising applying one or more amphiphile-producing microorganisms in a live or inactive form.

12. The method of claim 5, comprising covering the area of skin where the skin condition exists with a wound dressing that has been impregnated with the composition.

13. The composition of claim 1, further comprising a broth resulting from cultivation of a *Bacillus coagulans, Bacillus subtilis* or *Bacillus amyloliquefaciens* bacterium.

14. The wound dressing of claim 4, wherein the composition with which the wound dressing is impregnated further comprises a broth resulting from cultivation of a *Bacillus coagulans, Bacillus subtilis* or *Bacillus amyloliquefaciens* bacterium.

15. The method of claim 5, wherein the composition applied to the subject's skin further comprises a broth resulting from cultivation of a *Bacillus coagulans, Bacillus subtilis* or *Bacillus amyloliquefaciens* bacterium.

* * * * *